United States Patent
Hanafusa et al.

(10) Patent No.: US 9,523,791 B2
(45) Date of Patent: Dec. 20, 2016

(54) OBSERVATION DEVICE AND OBSERVATION MANAGEMENT SYSTEM

(71) Applicant: Casio Computer Co., Ltd., Tokyo (JP)

(72) Inventors: Norihito Hanafusa, Zushi (JP); Yukinori Ido, Tokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 0 days.

(21) Appl. No.: 14/814,041

(22) Filed: Jul. 30, 2015

(65) Prior Publication Data

US 2016/0041303 A1 Feb. 11, 2016

Related U.S. Application Data

(63) Continuation of application No. 13/396,876, filed on Feb. 15, 2012, now Pat. No. 9,128,213.

(30) Foreign Application Priority Data

Feb. 16, 2011 (JP) ................................. 2011-030395

(51) Int. Cl.
  *G01W 1/06* (2006.01)
  *G01N 33/24* (2006.01)
  *H04N 5/44* (2011.01)
  *H04N 7/18* (2006.01)

(52) U.S. Cl.
  CPC ............. *G01W 1/06* (2013.01); *G01N 33/246* (2013.01); *H04N 5/44* (2013.01); *H04N 7/185* (2013.01)

(58) Field of Classification Search
  None
  See application file for complete search history.

(56) References Cited

U.S. PATENT DOCUMENTS

| | | | |
|---|---|---|---|
| 2002/0167587 A1 | 11/2002 | Ogasawara | |
| 2007/0082600 A1* | 4/2007 | Asvestas | A01G 9/246 454/191 |
| 2008/0044529 A1 | 2/2008 | Yamashita | |
| 2008/0146936 A1* | 6/2008 | Furia | A61B 8/00 600/459 |

(Continued)

FOREIGN PATENT DOCUMENTS

| CN | 101790745 A | 7/2010 |
|---|---|---|
| JP | 2001204260 A | 7/2001 |

(Continued)

OTHER PUBLICATIONS

Japanese Office Action dated Dec. 2, 2014, issued in counterpart Japanese Application No. 2013-103725.

(Continued)

*Primary Examiner* — Eileen Adams
(74) *Attorney, Agent, or Firm* — Holtz, Holtz & Volek PC

(57) ABSTRACT

An observation device includes a handle having on a lower end side thereof an end portion including a tapered rod portion. The handle includes a protruding portion that protrudes outwardly from a side of the handle with respect to the tapered rod portion. The handle is formed so as to be held by a user to stick the rod portion into soil in a state that an index finger is applied on the handle from underneath and that a finger pad of a thumb presses against an upper end surface of the handle.

3 Claims, 13 Drawing Sheets

(56) References Cited

U.S. PATENT DOCUMENTS

| | | | |
|---|---|---|---|
| 2008/0202220 A1* | 8/2008 | Schmidt | A01G 25/167 73/75 |
| 2008/0247630 A1 | 10/2008 | Horiuchi | |
| 2010/0032546 A1 | 2/2010 | Kawano et al. | |
| 2010/0109946 A1 | 5/2010 | Pande | |
| 2010/0192683 A1* | 8/2010 | Elkins | E21B 47/00 73/152.18 |
| 2011/0279665 A1 | 11/2011 | Yamaguchi | |
| 2012/0029313 A1 | 2/2012 | Burdett et al. | |

FOREIGN PATENT DOCUMENTS

| | | |
|---|---|---|
| JP | 2003152621 A | 5/2003 |
| JP | 2005195341 A | 7/2005 |
| JP | 2006308493 A | 11/2006 |
| JP | 2006333744 A | 12/2006 |
| JP | 2007124932 A | 5/2007 |
| JP | 2008061575 A | 3/2008 |
| JP | 2008217702 A | 9/2008 |
| JP | 2010033326 A | 2/2010 |
| JP | 201075172 A | 4/2010 |
| JP | 2013162799 A | 8/2013 |

OTHER PUBLICATIONS

Extended European Search Report (EESR) dated May 14, 2013 (in English) issued in counterpart European Application No. 12155530.4.

Chinese Office Action dated Jan. 6, 2014 issued in Chinese Application No. 201210035229.X.

Japanese Office Action dated May 20, 2014, issued in counterpart Japanese Application No. 2013-103724.

Japanese Office Action dated Mar. 18, 2013 (and English translation thereof) in counterpart Japanese Application No. 2011-030395.

Kenshi Nishida et al.: "Sprouts: Plant Growth Support by Augmented Reality": Proceedings of 14th Workshop on Interactive Systems and Software (WISS 2006): pp. 23-26 (and English Abstract thereof).

Japanese Office Action (and English translation thereof) dated Mar. 1, 2016, issued in counterpart Japanese Application No. 2015-095319.

* cited by examiner

ENLARGED TAKEN IMAGE

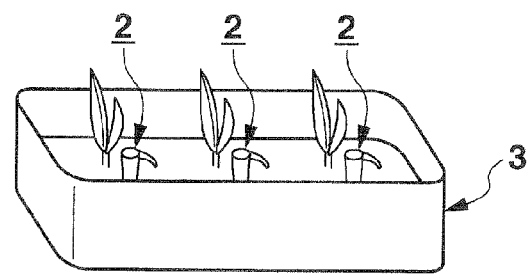
FIG.1C
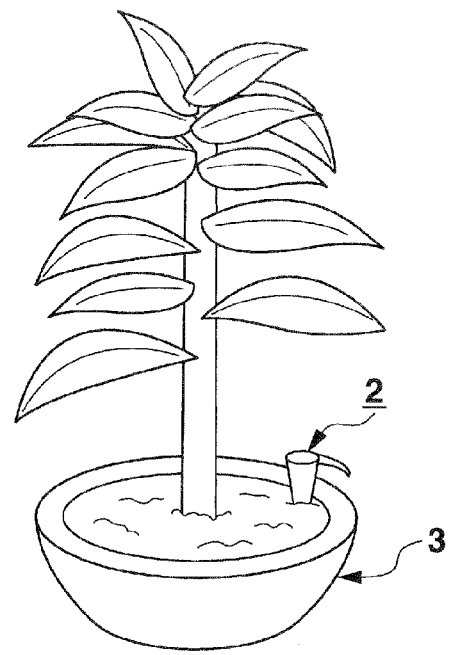
FIG.1D
FIG.2
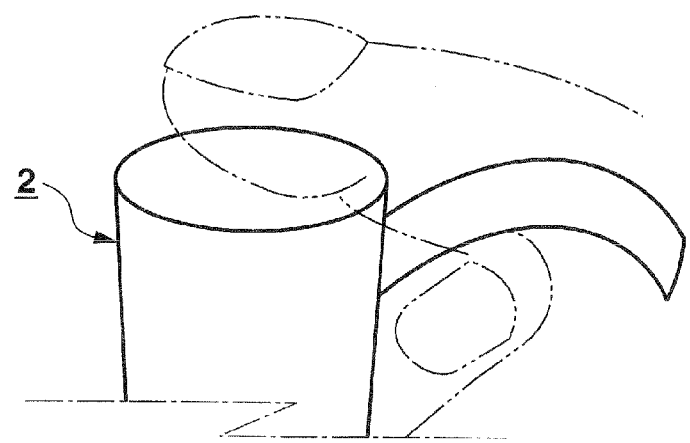

FIG.6

T1 OBSERVATION RESULT TABLE

| ID AND TYPE / DATE | OBSERVATION OBJECT ID | | | | |
|---|---|---|---|---|---|
| | No. 1 | No. 2 | No. 3 | No. 4 | No. 5 |
| | TYPE (CACTUS) | TYPE (VEGETABLE A) | TYPE (CYCLAMEN) | TYPE (FOLIAGE PLANT A) | TYPE (FOLIAGE PLANT B) |
| 20110117 OUTDOOR AIR TEMPERATURE | **** | **** | **** | **** | **** |
| OUTDOOR AIR HUMIDITY | **** | **** | **** | **** | **** |
| SOIL HUMIDITY | **** | **** | **** | **** | **** |
| SUNSHINE | **** | **** | **** | **** | **** |
| 20110115 | **** | **** | **** | **** | **** |
| 20110113 | **** | **** | **** | **** | **** |
| ... | ... | ... | ... | ... | ... |

FIG.7

T2 OPTIMAL ENVIRONMENTAL STATE TABLE

| TYPE | OPTIMAL ENVIRONMENTAL STATE | | | |
|---|---|---|---|---|
| | OUTDOOR AIR TEMPERATURE | OUTDOOR AIR HUMIDITY | SOIL HUMIDITY | SUNSHINE |
| CACTUS | **** | **** | **** | **** |
| FOLIAGE PLANT A | **** | **** | **** | **** |
| FOLIAGE PLANT B | **** | **** | **** | **** |
| CYCLAMEN | **** | **** | **** | **** |
| ... | ... | ... | ... | ... |

FIG.8
T3 CHARACTER IMAGE TABLE
| OPTIMAL | 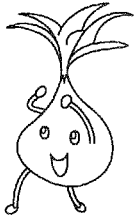 |
| EXCESSIVE SUNSHINE | 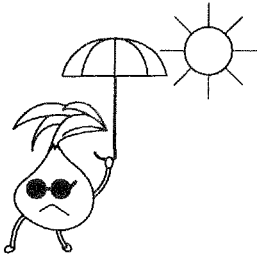 |
| INSUFFICIENT SOIL WATER | * * * * * * |
| ... | ... |

(OPTIMAL STATE)

TERMINAL SCREEN (EXCESSIVE SUNSHINE)

TERMINAL SCREEN

T6 OPTIMAL GROWTH STATE TABLE

| TYPE | OPTIMAL GROWTH STATE | | | |
|---|---|---|---|---|
| | NUMBER AND SIZE OF LEAVES | BLOOM CONDITION AND NUMBER OF FLOWERS | SIZE AND THICKNESS OF SHAFT | ... |
| CACTUS | * * * * | * * * * | * * * * | ... |
| FOLIAGE PLANT A | * * * * | * * * * | * * * * | ... |
| FOLIAGE PLANT B | * * * * | * * * * | * * * * | ... |
| CYCLAMEN | * * * * | * * * * | * * * * | ... |
| ... | ... | ... | ... | ... |

FIG.13

T7 PLANT TYPE TABLE

| TYPE | FEATURE INFORMATION | | | |
|---|---|---|---|---|
| | LEAF | SHAFT | FLOWER | ... |
| CACTUS | **** | **** | **** | ... |
| FOLIAGE PLANT A | **** | **** | **** | ... |
| FOLIAGE PLANT B | **** | **** | **** | ... |
| CYCLAMEN | **** | **** | **** | ... |
| ... | ... | ... | ... | ... |

OBSERVATION DEVICE AND OBSERVATION MANAGEMENT SYSTEM

CROSS-REFERENCE TO RELATED APPLICATIONS

This is a Continuation of U.S. application Ser. No. 13/396,876, filed Feb. 15, 2012, which is based upon and claims the benefit of priority from prior Japanese Patent Application No. 2011-030395, filed Feb. 16, 2011, the entire contents of both of which are incorporated herein by reference.

BACKGROUND OF THE INVENTION

1. Technical Field

Embodiments described herein relate to a portable device, an observation management system and a computer-readable medium.

2. Description of the Related Art

In general, when a plant is to be grown or cultivated, the amount of water supplied to the plant, the way of applying daylight, the way of applying fertilizer, the temperature condition, and the like to be employed depend on the plant type and the environment. Thus, there is disclosed a related-art technique that information necessary for growing a plant is provided to a user. For example, a technique (a plant growth guide system) discloses that an environment in which a plant is placed is observed by a sensor and then accumulated and managed, and that the observed environment is then compared with the optimal growth environment for the plant and then a guide for growth is displayed (see e.g., JP-A-2010-75172).

That is, the plant growth guide system has: a plant environment measuring unit provided in a pot placed outdoor; and a plant growth management unit (e.g., a personal computer) installed indoor. Then, in the plant environment measuring unit on the pot side, when a measurement switch is operated or alternatively a measurement time of day is reached, data measured by various kinds of sensors is saved. After that, when a communication switch on the measuring unit side is operated, the above-mentioned saved data is transmitted to the plant growth management unit in response to the operation. By using the received data and referring to a database, the management unit displays guide information serving as a treatment instruction.

The above-described related-art technique has a merit that an environmental measurement result of the plant is displayed so as to provide a help in glowing the plant. Nevertheless, it is uncertain that the display of guide information alone is sufficient for a user to appropriately determine the present state of the plant. Further, when the observation data is transmitted from the measuring unit to the management unit, the communication switch need be operated at each time. This requires time and effort from the user.

SUMMARY OF THE INVENTION

It is one of the illustrative aspects of the present invention to provide a portable device, an observation management system and a computer-readable medium configured to easily check the present state of the observation object at the site, without the necessity of a special operation, merely by taking an image of an observation object or its vicinity.

According to one or more illustrative aspects of the present invention, there is provided a portable device. The portable device includes: an image pick-up section that takes an image of an observation object or a vicinity of the observation object so as to obtain a taken image; a display section that displays the taken image; and a processor configured to: (a) acquire an observation result obtained by observing the observation object in the taken image, when the image pick-up section takes the image of the observation object or the vicinity of the observation object; (b) acquire state representation information that represents a present state of the observation object in accordance with the observation result; and (c) display the state representation information and the observation object in the display section.

Other aspects and advantages of the present invention will be apparent from the following description, the drawings and the claims.

BRIEF DESCRIPTION OF THE DRAWINGS

FIG. 1C is a diagram illustrating plural observation devices 2 stuck into a pot 3 for observing respective ones of plural observation objects;

FIG. 1D is a diagram illustrating a single observation device 2 stuck into a pot 3 for observing a single observation object;

FIG. 2 is a diagram explaining a way of holding an observation device 2 when the observation device 2 is to be stuck into or extracted from a pot 3;

FIG. 6 is a diagram describing an observation result table T1 provided on a portable device 1 side;

FIG. 7 is a diagram describing an optimal environmental state table T2 provided on a portable device 1 side;

FIG. 8 is a diagram describing a character image table T3 provided on a portable device 1 side;

FIG. 13 is a diagram describing a plant type table T7 provided in a storage section 13 of a portable device 1 according to a second embodiment.

DETAILED DESCRIPTION OF EXEMPLARY EMBODIMENTS

Exemplary embodiments of the present invention will be now described in detail with reference to the drawings.

(First Embodiment)

First, a first embodiment of the present invention will be now described below with reference to FIGS. 1A to 11.

Figure 1A:
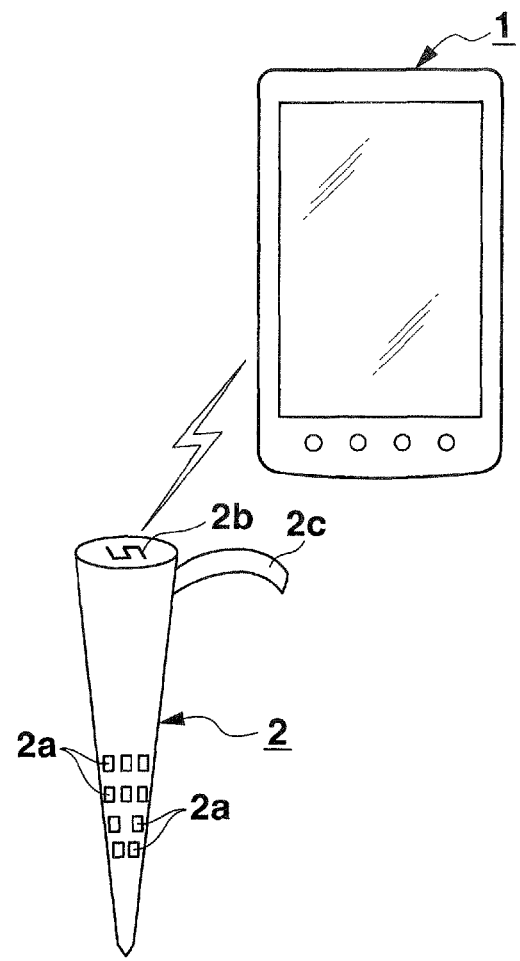
FIG. 1A is a block diagram showing an observation management system in which a portable device 1 having a camera function and an observation device 2 for observing an observation object are linked to each other by communication.
Figure 1B:
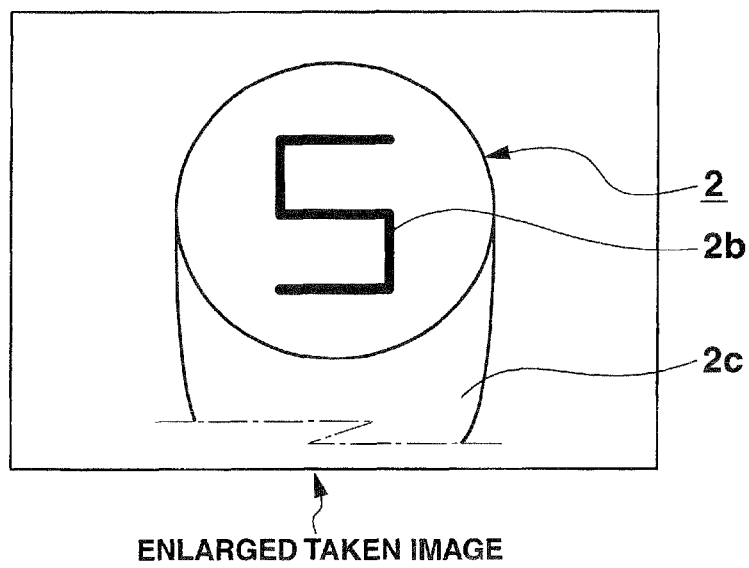
FIG. 1B is a diagram illustrating an exemplary enlarged image captured by a portable device 1 around an upper end surface of an observation device 2.

FIG. 1A is a block diagram showing an observation management system constructed such that a portable device 1 having a camera function and an observation device 2 for observing an observation object are linked to each other by communication.

The portable device 1 composed of a portable telephone has a voice call function, an electronic mail function, an Internet access function (a Web access function), an image pick-up function (a camera function), a short distance communication function, and the like, and performs transmission and reception of data to and from the observation device 2 by short distance communication.

The observation device 2 is used for observing the environment of an observation object (e.g., the growth environment of a plant such as a garden tree and a flower in the present embodiment). Its overall casing has the shape of an elongated hollow rod. Then, the overall hollow rod of the observation device 2 is formed in a tapered shape so that a lower part (e.g., the lower half) of the observation device 2 is buried into soil in a pot 3. Further, in the surface of the lower part, a plurality of pores 2a are formed for the purpose of aeration and water flow. Further, on the upper end surface of the observation device 2, an observation object ID (identification number "5" in the example shown) 2b used for identifying the observation object is formed by printing, stamping, or the like. Here, a user in a state of approaching the observation object takes an enlarged image around the upper end surface (the part of the observation object ID) of the observation device 2 by the camera function of the portable device 1 (see FIG. 1B).

Further, in one side part of the upper end part of the observation device 2, an arc-shaped handle 2c is formed in a protruding manner (molded integrally). Here, as shown in FIG. 2, when the lower part of the observation device 2 is to be stuck into or extracted from soil in the pot 3, sticking or extraction of the observation device 2 is smoothly achieved in a state that the finger pad of the thumb presses against the upper end surface and that the index finger is applied on the lower surface of the handle 2c. That is, the handle 2c is formed at a position that allows the casing to be stuck or extracted in a state that an index finger is applied on the handle 2c from the downside and that a finger pad of a thumb presses against an upper end surface of the casing.

Here, when a single garden tree or a single flower is planted in the pot 3 as shown in FIG. 1D, a single observation device 2 is stuck into the pot 3. Instead, when plural types of garden trees or flowers are planted in the pot 3 as shown in FIG. 1C, observation devices 2 in a number corresponding to the number of types are stuck into the pot 3.

Figure 3:
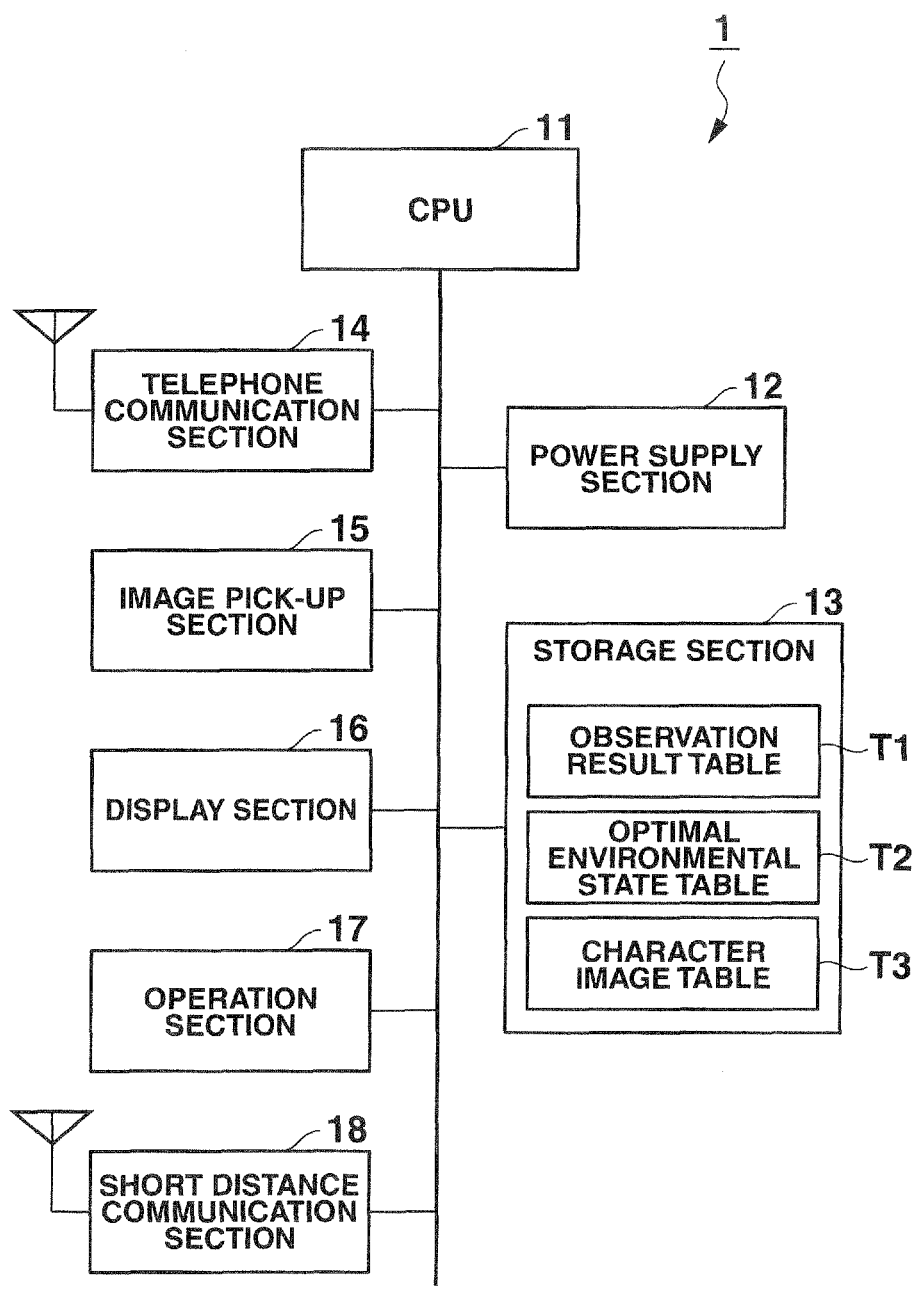
FIG. 3 is a block diagram showing basic components of a portable device 1.

FIG. 3 is a block diagram showing basic components of the portable device 1.

The CPU 11 is a central processing unit that operates by electric power supply from a power supply section 12 provided with a secondary battery (not shown) and that controls the overall operation of the portable device 1 in accordance with various kinds of programs in a storage section 13. The storage section 13 stores a program for implementing the present embodiment in accordance with the operation procedure shown in FIG. 9 and stores various kinds of applications. In addition, the storage section 13 has a work area used for temporarily storing various kinds of information necessary in the operation of the portable device 1 and also has an observation result table T1, an optimal environmental state table T2, a character image table T3, and the like, which are described later.

The telephone communication section 14 is a broader-based communication section used for a voice call function, an electronic mail function, and an Internet access function. The image pick-up section 15 constitutes a camera section capable of taking a high definition image of a photographic object, and has an optical lens, an image sensor, an optical-system driving section, a stroboscope for illumination, an analog processing circuit, a signal processing circuit, and the like (not shown). Then, the image pick-up section 15 adjusts and controls optical zoom, and controls auto-focusing drive, shutter drive, exposure, balance, and the like.

The display section 16 is constructed from a high definition liquid crystal display, an organic EL display, an electrophoresis type display (an electronic paper), or the like, and displays display information including text information and a standby image. Further, at the time of use of a camera function, the display section 16 serves as a finder screen for displaying a live view image (a monitor image) as a taken image. On the surface of the display section 16, a contact operation section (a transparent contact sensor) for detecting the contact of a finger is stacked so that a touch screen is constructed. Here, the display section 16 is arranged in a front part of the portable device 1, whereas the image pick-up section 15 is arranged in a rear part of the portable device 1. The operation section 17 has a power ON/OFF button, a button used for switching the mode to a camera monitor mode, and the like (not shown). Then, the CPU 11 performs processing in accordance with the operation buttons.

The short distance communication section 18 constitutes a Bluetooth (registered trademark) module for performing communication with the observation device 2, and operates within a communication available area (e.g., within a radius of 2 m). A search signal for searching for the observation device 2 is transmitted from the portable device 1. Then, when a response to this is obtained, communication link between the portable device 1 and the observation device 2 is established and hence data communication to each other is allowed. In this case, the portable device 1 receives and acquires an observation result transmitted from the observation device 2.

Figure 4:
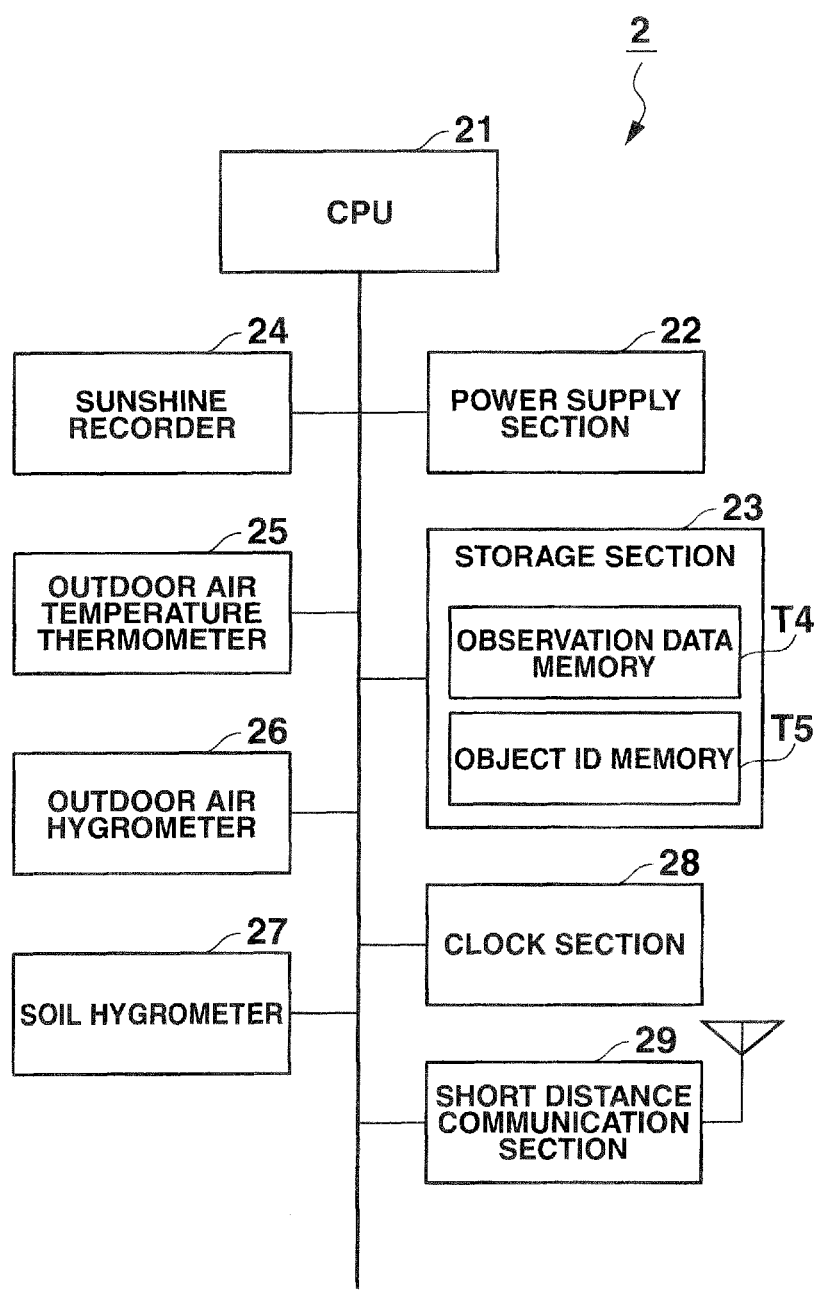
FIG. 4 is a block diagram showing basic components of an observation device 2.

FIG. 4 is a block diagram showing basic components of the observation device 2.

The CPU 21 operates by electric power supply from a power supply section 22 provided with a battery (a primary battery or a secondary battery), and controls the overall operation of the observation device 2 in accordance with various kinds of programs in the storage section 23. The storage section 23 has an observation data memory T4 and an object ID memory T5 described later. Further, the CPU 21 is connected to observation sections (various kinds of environment sensors) composed of I/O devices such as a sunshine recorder 24 for measuring a sunshine condition, an outdoor air temperature thermometer 25 for measuring outdoor air temperature, an outdoor air hygrometer 26 for measuring outdoor air humidity, a soil hygrometer 27 for measuring humidity on the surface of the soil in the pot 3. The CPU 21 is further connected to a clock section 28 for measuring the present date and time and a short distance communication section 29 for performing short distance radio communication with the portable device 1 (Bluetooth communication). Here, each of the sunshine recorder 24, the outdoor air temperature thermometer 25, the outdoor air hygrometer 26, and the soil hygrometer 27 is a small electronic component capable of precision measurement. However, their configuration is widely known, and hence their description is omitted.

At each time interval (e.g., every day and every two days) set up in advance, the CPU 21 of the observation device 2 acquires growth environment (an observation result) observed by the sunshine recorder 24, the outdoor air temperature thermometer 25, the outdoor air hygrometer 26, and the soil hygrometer 27. Then, the growth environment (observation result) is stored and added into the observation data memory T4 in a manner of correspondence to the present date and time obtained from the clock section 28. Further, when communication link is established between the portable device 1 and the observation device 2 through the short distance communication section 29, the CPU 21 reads the contents of the object ID memory T5 and the observation data memory T4, and then transmits the data through the short distance communication section 29 to the portable device 1. The object ID memory T5 is a memory for storing an observation object ID (identification number "5" in the example in FIGS. 1A and 1B). The observation data memory T4 is a memory for storing the observation result (the observation result concerning growth environment) obtained by the sunshine recorder 24, the outdoor air temperature thermometer 25, the outdoor air hygrometer 26, and the soil hygrometer 27.

Figure 5:
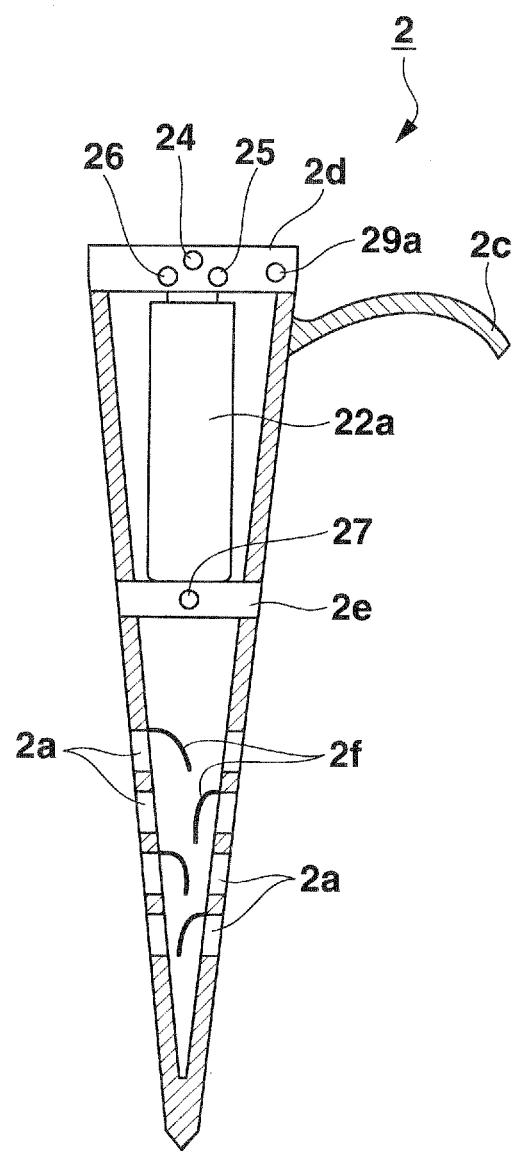
FIG. 5 is a schematic vertical sectional view of an observation device 2.

FIG. 5 is a schematic vertical sectional view of the observation device 2.

The top plate section 2d on the upper end side of the observation device 2 incorporates various kinds of electronic components such as the sunshine recorder 24, the outdoor air temperature thermometer 25, the outdoor air hygrometer 26, and an antenna 29a for the short distance communication section 29. Further, under these electronic components, a battery 22a serving as the power supply section 22 is built in. Further, the center partition board 2e of the observation device 2 incorporates the soil hygrometer 27. Further, in the surface on the lower end side of the observation device 2, the plurality of pores 2a described above are formed for the purpose of aeration and water flow. Then, in the hollow part on the lower end side of the observation device 2, a plurality of valve members 2f for preventing entrance of soil thereinto are formed in the parts where the pores 2a are performed. Here, although not shown in the figure, the upper half part and the lower half part of the observation device 2 are separable from each other at the center partition board 2e, and hence the lower half part of the observation device 2 can be changed suitably. Here, when the upper half part and the lower half part of the observation device 2 are separated from each other, a cassette of nutrient ampule may be inserted into the hollow part in the lower half part so that nutrient may be injected into soil.

FIG. 6 is a diagram describing the observation result table T1 provided on the portable device 1 side.

The observation result table T1 is a table in which the observation results (observation results concerning growth environment) transmitted from the observation device 2 are stored and managed for each date of observation and for each observation object ID. In the figure, the vertical direction in the table corresponds to the "date of observation", and the horizontal direction corresponds to the "observation object ID". In the example shown, "No. 1", "No. 2", "No. 3", "No. 4", "No. 5", . . . indicate observation object IDs assigned to a plurality of the observation devices 2. A plant type is stored in correspondence to each observation object ID, like "cactus" for "No. 1", "vegetable A" for "No. 2", "cyclamen" for "No. 3", "foliage plant A" for "No. 4", "foliage plant B" for "No. 5", . . . Here, the correspondence between the observation object ID and the plant type is arbitrarily set up by user's operation.

Further, in the storage area where the "date of observation" and the "observation object ID" intersect with each other in the observation result table T1, the outdoor air temperature, the outdoor air humidity, the soil humidity, and the sunshine are stored as the observation result for the observation object received from the observation device 2. In this case, the observation result table T1 stores the observation result data for a predetermined number of past days (e.g., one month). Then, in a full storage state that the observation result data for the predetermined number of days has already been stored, for example, older observation result data is deleted in a first-in first-out manner.

FIG. 7 is a diagram describing the optimal environmental state table T2 provided on the portable device 1 side.

The optimal environmental state table T2 is a table used for storing and managing the optimal environmental state for the growth of each type of observation object, and stores for each plant type the optimal state (a particular state) of the outdoor air temperature, the outdoor air humidity, the soil humidity, and the sunshine. For example, in the setup for the optimal environment concerning the temperature for cyclamen, the outdoor air temperature is 25° C., the cold-resistance temperature is 7° C., and the growth appropriate temperature (the optimum temperature range) is 15° C. to 25° C. The optimal environment is defined time-dependently along the time cycle from January to December. Further, the optimal environment also includes information concerning the optimal timing for additional fertilization, division, pot change, and the like.

FIG. 8 is a diagram describing the character image table T3 provided on the portable device 1 side.

The character image table T3 is a table used for storing and managing state representation information (a predetermined pictorial diagram such as a character image) that represents the present state of an observation object in accordance with the observation result of the observation object. The character image table T3 is used when a character image is to be identified in accordance with the observation result of the observation object. That is, the character image table T3 stores character images of the contents representing the states of "insufficient water", "excessive water", "excessive sunshine", and the like selected in accordance with the present state of the observation object. Here, in the examples shown, the character image table stores: a character image indicating that the growth environment of water, humidity, and sunshine is "optimal"; and a character image indicating that the environment is "excessive sunshine".

Figure 9:
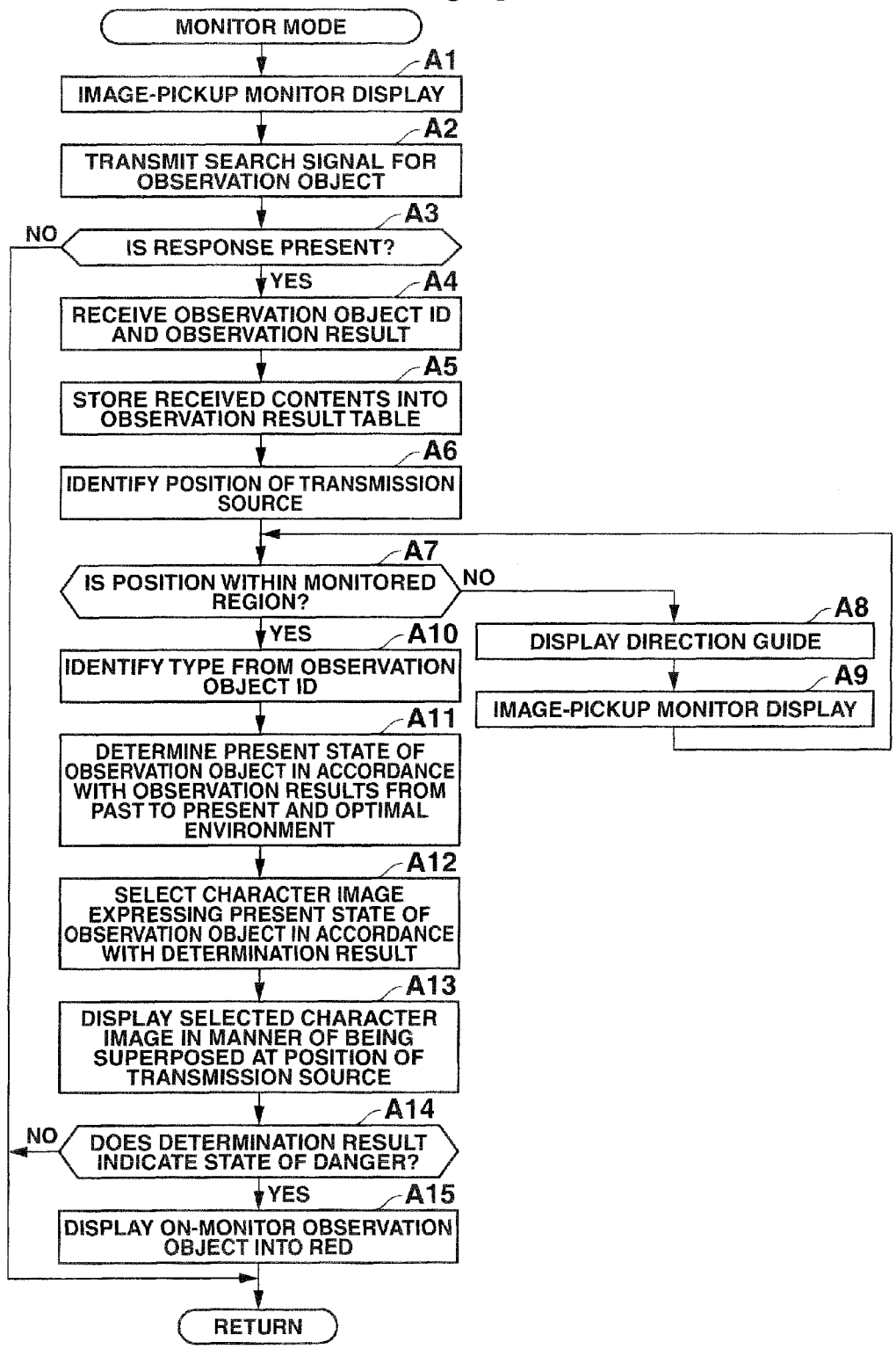
FIG. 9 is a flow chart of a procedure started and executed when a mode is changed to a camera monitor mode that a through image (a taken image) from an image pick-up section 15 is displayed as a monitor image.

Next, the concept of operation of the portable device 1 according to the first embodiment is described below with reference to the flow chart shown in FIG. 9. Here, each function described in the flow chart is stored in the form of a computer-readable program code. Then, operation is serially executed in accordance with the program code. Further, operation may be serially executed in accordance with the above-mentioned program code transmitted through a transmission media such as a network. This situation is similar in other embodiments described later. That is, in addition to a recording medium, the operation specific to the present embodiment may also be executed in accordance with a program or data provided from the outside through a transmission medium. Here, FIG. 9 is a flow chart showing the outline of operation constituting the feature of the present embodiment among the overall operation of the portable device 1. When the procedure goes out from the flow in FIG. 9, the procedure returns to the main flow (not shown) of overall operation.

FIG. 9 is a flow chart of a procedure started and executed when the mode is changed to a camera monitor mode that a through image (a taken image) from the image pick-up section 15 is displayed as a monitor image. In the monitor mode, the user directs the image pick-up section 15 toward the observation object or its vicinity.

First, the CPU 11 performs image pick-up monitor display in which a through image is acquired from the image pick-up section 15 and then is displayed as a monitor image on the display section 16 (step A1). Then, the short distance communication section 18 is started so as to transmit a search signal for searching for the observation device 2 (step A2).

In this state, the presence or absence of a response from the observation device 2 to the search signal is checked (step A3). Then, in a case that no response is obtained from the observation device 2 even when a predetermined time has elapsed (NO at step A3), the procedure escapes from the flow of FIG. 9 at this time. In contrast, when a response is received from the observation device 2 (YES at step A3), a communication available state is realized that communication is established between the portable device 1 and the observation device 2. In this state, when an observation result (an observation result concerning growth environment) together with the observation object ID is received and acquired from the observation device 2 (step A4), the received contents (the observation object ID and the observation result) are stored and added into the observation result table T1 (step A5).

Then, the processing of identifying the position of the transmission source, that is, the processing of analyzing the receiving condition (radio wave intensity and the like) of the radio waves so as to identify the approximate position of the transmission source (the observation device 2) having transmitted the observation object ID (step A6). Then, it is checked whether the identified position falls within the region of monitor image taking (whether the transmission source is located within the monitor image) (step A7). Then, when the position falls outside the region of monitor image taking (NO at step A7), a direction guide for guiding the direction to the region of monitor image taking is displayed on the display section 16 (step A8). Then, in a state that image pick-up monitor display in which a through image is displayed as a monitor image is performed (step A9), the procedure returns to the above-mentioned step A7 and hence it is checked whether the position of the transmission source has entered the region of monitor image taking.

When the position of the transmission source falls within the region of monitor image taking or alternatively has entered the region (YES at step A7), the observation result table T1 is searched on the basis of the observation object ID so that the type of observation object (plant) corresponding to the observation object ID is identified (step A10). Then, with reference to the contents of the observation result table T1 corresponding to the observation object ID (or the plant type) and the contents of the optimal environmental state table T2, the state of change from the past observation result to the present observation result is determined as the present state of the observation object (step A11). For example, the present state of the observation object (the plant) is determined that: (1) "the state of insufficient water has continued for many days (insufficient water)" in comparison with the optimal environmental state for the foliage plant A; (2) "the state of excessive water has continued for many days (excessive water)" in comparison with the optimal environmental state for the cactus; (3) "the state of excessive sunshine has continued for many days (excessive sunshine)" in comparison with the optimal environmental state for the vegetable A; or (4) "the environment is optimal for the cactus".

Then, state representation information is acquired that represents the present state of the observation object. That is, on the basis of the above-mentioned determination result (e.g., "insufficient water", "excessive water", and "excessive sunshine"), the character image table T3 is searched so that a corresponding character image is selected, read, and acquired (step A12). Then, the selected character image is displayed and superposed at a position of the transmission source (the observation device 2) in the monitor image (step A13). After that, it is determined whether the above-mentioned determination result (the present state of the observation object) is of a state indicating a particular situation, that is, a state of danger, which means a state that "insufficient water", "excessive water", "excessive sunshine", or the like has continued for an unusually long time (step A14).

Figure 10:
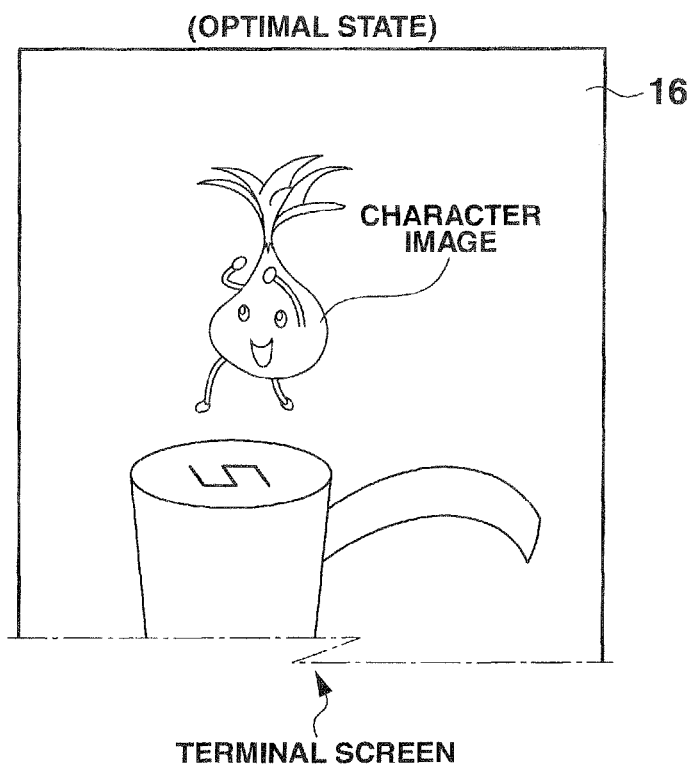
FIG. 10 is a diagram showing an example of character image display used when the present state of an observation object (plant) is optimal.
Figure 11:
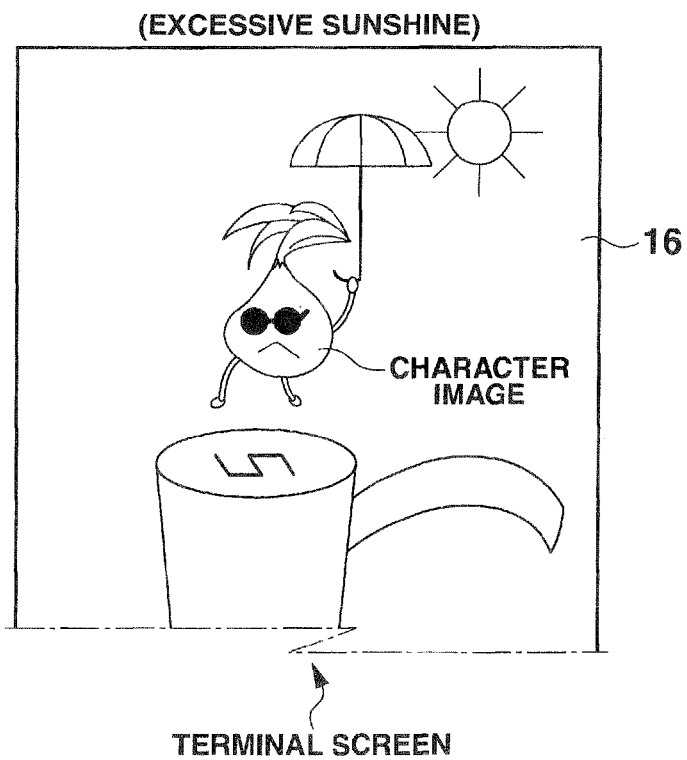
FIG. 11 is a diagram showing an example of character image display used when the present state of an observation object (plant) is of excessive sunshine.

When the present state of the observation object is not of a state of danger (NO at step A14), the procedure goes out from the flow of FIG. 9 at that time. In contrast, in a case of a state of danger (YES at step A14), the part of the image of the observation object identified by analyzing the monitor image is identified (in red) and displayed (step A15). Then, the procedure goes out from the flow of FIG. 9. Here, FIG. 10 is a diagram showing an example of character image display performed when the determination result is optimal. FIG. 11 is a diagram showing an example of character image display performed when the determination result is of excessive sunshine, in which the upper end part of the observation device 2 and a character image are shown in the monitor image. Here, in FIGS. 10 and 11, the character image and a part of the observation device 2 are shown solely, and the observation objects, the pot 3, and the like are omitted.

As described above, in the first embodiment, when an image of the observation object or its vicinity is taken by the image pick-up section 15, the portable device 1 acquires an observation result of the observation object in the taken image (the monitor image). Further, after acquiring the state representation information that represents the present state of the observation object in accordance with the acquired observation result, the portable device 1 displays onto the display section 16 the state representation information in a manner of correspondence to the observation object in the taken image. Thus, without the necessity of special operation, merely by taking an image of the observation object, the user can easily check the present state of the observation object at the site (near the observation object). This provides convenience.

The portable device 1 receives and acquires by short distance communication the type of the observation object and its observation result transmitted from the observation device 2, and then determines the present state of the observation object in accordance with the result of comparison between the contents of the optimal environmental state table T2 corresponding to the type of the observation object and the acquired observation result. Thus, the present state can be determined for each observation object type.

With adopting a plant as an observation object, the portable device 1 receives and acquires an observation result concerning the observed growth observed by the environment sensors (the sunshine recorder 24, the outdoor air temperature thermometer 25, the outdoor air hygrometer 26, and the soil hygrometer 27) provided on the plant side. Thus, on the basis of the observation result, the present state of the plant can be determined appropriately.

The portable device 1 transmits a search signal for searching for the observation object (the observation device 2) by short distance communication and then receives and acquires an observation result transmitted from the observation device 2 side in response to the search signal. Thus, the observation result is acquired merely by approaching the observation object (the observation device 2).

The portable device 1 acquires a predetermined pictorial diagram (a character image) as state representation information expressing the present state of the observation object. This allows the user to recognize the present state of the observation object through an intuitively simple expression.

The portable device 1 acquires state representation information that represents the present state of the observation object in accordance with the state of change from the past observation result to the present observation result of the observation object. Thus, the present state is determined appropriately and corresponding state representation information is acquired.

When the present state of the observation object is of a state indicating a particular situation (e.g., a state of danger), the portable device 1 performs display that specifies the particular state (e.g., display in red). Thus, the particular state is notified reliably.

The state representation information is displayed and superposed at the position of the observation object in the taken image. This clarifies the correspondence between the state representation information and the observation object.

In the observation management system constructed such that the portable device 1 and the observation device 2 are linked to each other by communication, the observation device 2 transmits by short distance communication an observation result in response to a search signal for searching for an observation object transmitted from the portable device 1. Further, when an image of the observation object is taken by the image pick-up section 15, the portable device 1 in response to the search signal receives and acquires the observation result of the observation object transmitted from the observation device 2 by short distance communication, then acquires state representation information that represents the present state of the observation object in accordance with the acquired observation result, and then displays the state representation information onto the display section 16 in a manner of correspondence to the observation object in the taken image. Thus, without the necessity of special operation, merely by taking an image of the observation object, the user can easily check the present state of the observation object at the site (near the observation object). This provides convenience.

The observation device 2 is stuck and extracted in a state that the index finger is applied on the handle 2c from the downside and that the finger pad of the thumb presses against the upper end surface of the casing. Thus, sticking and extraction are achieved smoothly.

In the first embodiment described above, Bluetooth communication has been employed between the portable device 1 and the observation device 2. However, employable configurations are not limited to this. That is, short distance communications such as infrared communication and non-contact ID card communication may be employed. Further, in place of such short distance communication, communication between the portable device 1 and the observation device 2 may be implemented through a local area network or a wide area network.

In the first embodiment described above, the state representation information that represents the present state of the observation object has been read and acquired from the character image table T3. Instead, the state representation information may be received and acquired from a server device (not shown) via a local area network or a wide area network.

(Second Embodiment)

A second embodiment of the present invention will be now described below with reference to FIGS. 12 to 14.

Here, in the first embodiment described above, the portable device 1 has received and acquired an observation result together with an observation object ID from the observation device 2 by short distance communication, and then has determined as the present state of the observation object the state of change from the past to the present observation result corresponding to the observation object ID (the plant type). In contrast, in the second embodiment, the portable device 1 analyzes a monitor image so as to acquire the type of the observation object and its observation result by image recognition, and then determines the present state of the observation object in accordance with a result of comparison between the observation result and the optimal state corresponding to the type of the observation object. Here, in the two embodiments, basically or literally like components are denoted by like numerals and their description is omitted. Thus, the following description is given mainly for the features of the second embodiment.

Figure 12:
FIG. 12 is a diagram describing an optimal growth state table T6 provided in a storage section 13 of a portable device 1 according to a second embodiment.

FIG. 12 is a diagram describing an optimal growth state table T6 provided in the storage section 13 of the portable device 1 according to the second embodiment.

The optimal growth state table T6 is a table for storing color, growth, bloom condition, and the like for each plant type. In this table, the growth optimal state for "number and size of leaves", "bloom condition and number of flowers", "size and thickness of shaft", . . . are stored in correspondence to each observation object (plant) type. Then, in the optimal growth state table T6, for example, the optimal growth state is stored for each plant type for each growth stage such as a sowing stage, a raising seedling stage, and a flowering stage, and for each season.

FIG. 13 is a diagram describing a plant type table T7 provided in the storage section 13 of the portable device 1 according to the second embodiment.

The plant type table T7 stores information describing the features of a plant of each type, and is used for identifying a plant type. In the example shown, the features of the individual parts of each plant type are described by the items of "leaf", "stalk", "flower", . . . . Each item describes feature information such as the color and the flower shape along the growth stage.

Figure 14:
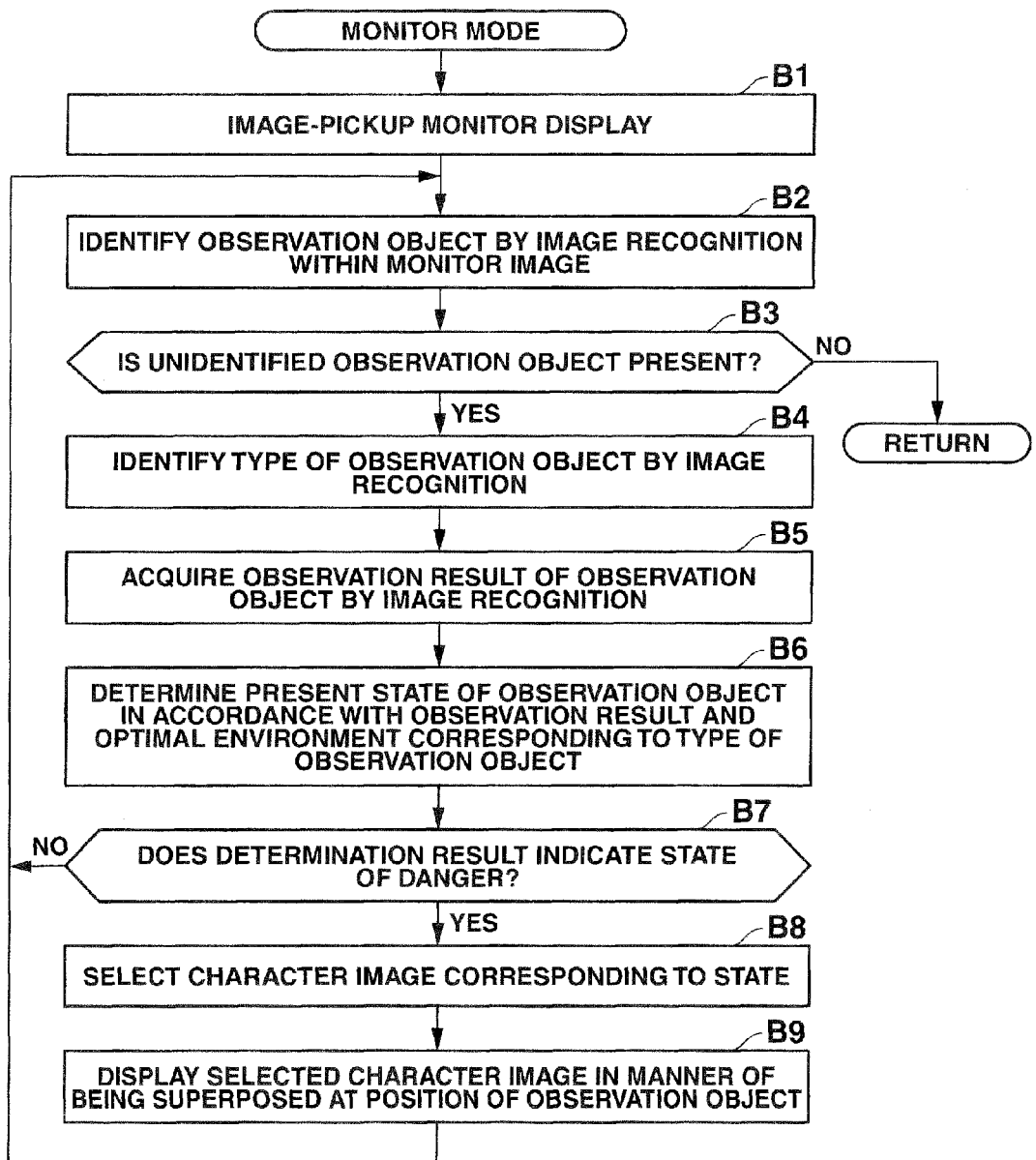
FIG. 14 is a flow chart of a procedure started and executed when a mode is changed to a camera monitor mode according to the second embodiment.

FIG. 14 is a flow chart of a procedure started and executed when the mode is changed to a camera monitor mode according to the second embodiment.

First, the CPU 11 performs image pick-up monitor display in which a through image is acquired from the image pick-up section 15 and then is displayed as a monitor image on the display section 16 (step B1). Then, image recognition is performed on the monitor image so that the observation object is identified (step B2). Here, the second embodiment employs a well-known image recognition technique. Thus, its detailed description is omitted. However, the image region of the observation object is comprehensively determined by taking into consideration the shape and the color of the plant as well as the relation with the surrounding pot and the like. Further, when a plurality of observation objects are present in the monitor image, each observation object is identified separately.

As a result of the image recognition, it is checked whether an unidentified observation object which is not yet identified as an observation object is contained in the monitor image (step B3). When no unidentified object is contained (NO at step B3), the procedure goes out from the flow of FIG. 14. In contrast, when an unidentified object is contained (YES at step B3), image recognition is performed further so that a type (e.g., a cactus and a foliage plant A) is identified for each identified observation object (step B4). In this case, with reference to the contents of the plant type table T7, it is checked whether a photographic object (a plant) having a feature similar to the feature information of a plant is contained in the monitor image. Then, when a photographic object having a similar feature is included, the type is identified. For each observation object, the color, the growth, the bloom condition, and the like of the plant are observed comprehensively by image recognition so that an observation result is obtained (step B5).

As such, the present state of the observation object is determined on the basis of the contents of the optimal growth state table T6 corresponding to the type of the identified observation object and on the basis of the observation result (step B6). For example, it is determined that "in comparison with the optimal growth state, blooming is delayed by about one week", "the number of flowers is few", or the like. Then, it is checked whether this determination result is of a state indicating a particular situation, that is, of a state of danger that is far from the optimal state, like of a state that the growth is in danger of insufficient fertilizer, excessive sunshine, or the like (step B7). In contrast, when in a case of not being in a state of danger (NO at step B7), the procedure returns to the above-mentioned step B2 so that the presence or absence of another unidentified object is checked.

Further, when the present state of the observation object is of a state of danger (YES at step B7), a character image representing this state is selected (step B8). Then, the selected character image is displayed and superposed at the position of the observation object in the monitor image (step B9). Here, in the second embodiment, when the position of display of the character image is touched, detailed information concerning the growth is popup-displayed. After that, the procedure returns to the above-mentioned step B2. Then, when an unidentified object is present in the monitor image (YES at step B3), the above-mentioned operation is repeated. As a result, the operation of, when the present state of the observation object is of a state of danger that is far from the optimal state, displaying a character image expressing a state of danger in a manner of correspondence to the observation object in the through image is repeated for each observation object.

As described above, in the second embodiment, the portable device 1 analyzes a monitor image taken by the image pick-up section 15 and observes the observation object in the monitor image so as to acquire an observation result. Thus, without the necessity of a special device on the observation object side, merely by taking an image of the observation object, the present state of the observation object is easily checked at the site.

Further, a taken image is analyzed and an observation object in the taken image is observed so that its type and its observation result are acquired by image recognition. After that, the contents of the optimal growth state table T6 corresponding to the type of the observation object are compared with the acquired observation result so that the present state of the observation object is determined in accordance with the comparison result. Thus, the present state can be determined for each observation object type.

When an image of a plurality of observation objects is taken, a through image is analyzed and each observation object is observed so that an observation result is acquired. Then, when comparison of the observation result acquired for each observation object with the optimal state in the optimal growth state table T6 indicates a state of danger, state representation information representing this state is displayed in a manner of correspondence to the observation object in the through image. Thus, observation objects in a state of danger are solely selected from the plurality of observation objects and then state representation information is displayed in the through image in a manner of correspondence to the observation object. This allows the user to easily and reliably find observation objects in a state of danger.

Here, in each embodiment described above, an augmented reality (AR) technique may be combined with the camera function so that the user may be advised by physical feeling or by experience. In this case, a personified AR character image may be employed for advice presentation so that a plant accurately not capable of expressing intention may be represented as if it had intention and personality. This provides to the user: an affectional value that the feeling of a plant is virtually experienced through a character image; and a practical value that a difficulty in plant growth and management is alleviated. As such, since an AR character image is displayed exactly in the same space as the plant (the observation object), such expression is achievable as if the plant had intention and personality. Here, it may be checked by image recognition whether the plant (the observation object) is located within the through image. Then, only when the plant is located within the image, the AR character image may be displayed together with the plant.

Further, in each embodiment described above, a plant has been employed as an observation object. The present invention may be applied to an object which is favored as a hobby and whose optimality or inappropriateness in the situation cannot be determined easily, like a water tank environment in an aquarium, a bird such as a parakeet and a Java sparrow, and an automobile. In this case, when a pet animal or a tropical fish is adopted as the observation object, the environment of a breeding room for the pet, the water tank environment, or the like may be observed. The observation device 2 may be provided in the collar of a dog or a cat. Alternatively, the observation device 2 may be provided in the water tank. However, employable configurations are not limited to these. Further, employable observation objects are not limited to a living thing such as a pet, and may be a perishable food such as meat and vegetable. Then, the storage environment of a refrigerator or a storage place, or alternatively the state of freshness may be observed. Alternatively, the chamber environment of a closet or the like may be observed. That is, the employed observation object is arbitrary.

In each embodiment described above, a character image has been displayed as state representation information. However, employable configurations are not limited to this. That is, other pictorial diagrams such as an icon having rich power of expression may be employed. Further, an advice balloon or the like may be employed as the state representation information. In each embodiment described above, when state representation information is to be displayed in a manner of correspondence to the position of display of the observation object, the state representation information has been superposed at the position of display of the observation object. However, employable configurations are not limited to such superposition display as long as correspondence between the observation object and the state representation information is clear.

In each embodiment described above, the optimal environmental information has been stored in the optimal environmental state table T2 and the optimal growth state has been stored in the optimal growth state table T6. However, information to be stored is not limited to an optimal one. That is, for example, the worst state or an unsuitable state may be stored.

Further, in each embodiment described above, the state representation information (the character image) in the through image may be saved as a taken image. That is, the state representation information (the character image) may be combined into the through image, and then the combined image may be recorded and saved.

Further, in each embodiment described above, the observation device 2 has been provided with the sunshine recorder 24, the outdoor air temperature thermometer 25, the outdoor air hygrometer 26, and the soil hygrometer 27. In addition, a soil water measuring instrument (not shown) for detecting a soil water content may be provided further. In this case, an electrode may be provided in the outer peripheral surface of the lower end part of the observation device 2 so that the water content may be measured directly on the basis of the electric current. Further, an instrument for measuring the pH (the acidity) or the amount of ions in the soil may be provided in the hollow part in the lower half part of the observation device 2.

Further, each embodiment described above has been given for a case that the present invention is applied to the portable device 1. However, the application is not limited to the portable device 1, and may be a PDA, a digital camera, a music player, or the like having a camera function. Obviously, the application may be a digital camera itself.

Further, each "device" or each "section" described in each embodiment described above may be separated into a plurality of casings for each function, and hence may be not contained in a single casing. Further, each step described in each flow chart described above need not be processed serially in time. That is, a plurality of steps may be processed in parallel, or alternatively may be processed separately and independently.

While the present invention has been shown and described with reference to certain exemplary embodiments thereof, other implementations are within the scope of the claims. It will be understood by those skilled in the art that various changes in form and details may be made therein without departing from the spirit and scope of the invention as defined by the appended claims.

The invention claimed is:

1. An observation management system comprising:
  a portable device; and
  an observation device that observes an observation object and that communicates with the portable device,
  wherein the observation device comprises:
    at least one observation section;
    a handle having on a lower end side thereof an end portion comprising a tapered rod portion, the handle comprising a protruding portion that protrudes outwardly from a side of the handle with respect to the tapered rod portion, wherein the handle is formed so as to be held by a user to stick the rod portion into soil in a state that an index finger is applied on the handle from underneath and that a finger pad of a thumb presses against an upper end surface of the handle;
    a designating section that designates observation object identification information that identifies a type of the observation object from among a plurality of types of observation objects; and
    a transmitting section that transmits an observation result of the at least one observation section to the portable device by wireless communication, and
  wherein the portable device comprises:
    an image pick-up section, wherein the portable device identifies the type of the observation object by analyzing an image which is picked-up by the image pick-up section; and
    an observation result table that receives the observation result from the observation device by the wireless communication and that manages observation results for each of the plurality of types of observation objects.

2. The observation management system according to claim 1, wherein the portable device further comprises an environmental state table that stores an optimal environmental state for each of the plurality of types of observation objects.

3. The observation management system according to claim 1, wherein a correspondence between the observation object identification information and the type of the observation object is set by a user operation.

* * * * *